United States Patent
Seibert et al.

(10) Patent No.: US 7,235,671 B2
(45) Date of Patent: Jun. 26, 2007

(54) PROCESS FOR PREPARING 3-CHLOROMETHYL-1,2,4-TRIAZOLIN-5-ONE

(75) Inventors: Kevin Seibert, Hillsborough, NJ (US); Clinton Scott Shultz, Maplewood, NJ (US); David M. Tellers, Cranford, NJ (US)

(73) Assignee: Merck & Co. Inc., Rahway, NJ (US)

( * ) Notice: Subject to any disclaimer, the term of this patent is extended or adjusted under 35 U.S.C. 154(b) by 23 days.

(21) Appl. No.: 10/524,866

(22) PCT Filed: Aug. 18, 2003

(86) PCT No.: PCT/US03/25679

§ 371 (c)(1),
(2), (4) Date: Feb. 14, 2005

(87) PCT Pub. No.: WO2004/017898

PCT Pub. Date: Mar. 4, 2004

(65) Prior Publication Data

US 2006/0052355 A1    Mar. 9, 2006

Related U.S. Application Data

(60) Provisional application No. 60/404,843, filed on Aug. 21, 2002.

(51) Int. Cl.
*C07D 249/12* (2006.01)
*C07C 281/06* (2006.01)

(52) U.S. Cl. ..................................... 548/263.2; 564/34

(58) Field of Classification Search .............. 548/263.2
See application file for complete search history.

(56) References Cited

U.S. PATENT DOCUMENTS

| 2,749,217 A | 6/1956 | Deutschman, Jr. |
| 6,297,376 B1 | 10/2001 | Cottrell et al. |
| 6,407,255 B2 | 6/2002 | Cottrell et al. |

FOREIGN PATENT DOCUMENTS

| WO | WO 99/65900 | 12/1999 |
| WO | WO 01/96315 | 6/2001 |

OTHER PUBLICATIONS

*Journal of the American Chemical Society*, 41, 393 (1919) "The Relations Between The Chemical Structures of Carbonyl Derivatives and Their Reactivities Toward Salts of Semicarbazide".
*Journal of the American Chemical Society*, 52, 1250 (1930) "The Preparation of Semicarbazide".
*Tetrahedron Letters*, 41 (2000) 8661-8664 "A New Synthesis of 1,2,4-triazolin-5-ones: application to the convergent synthesis of a NKI antagonist".

*Primary Examiner*—Venkataraman Balasubramanian
(74) *Attorney, Agent, or Firm*—J. Eric Thies; William Krovatin

(57) ABSTRACT

The present invention is directed to processes for the preparation of 3-chloromethyl-1,2,4-triazolin-5-one. This compound is useful as an intermediate in the synthesis of compounds which possess pharmacological activity. Also disclosed are novel semicarbazide salts and the preparation thereof, which are intermediates for the preparation of 3-chloromethyl-1,2,4-triazolin-5-one.

15 Claims, No Drawings

PROCESS FOR PREPARING 3-CHLOROMETHYL-1,2,4-TRIAZOLIN-5-ONE

CROSS REFERENCE TO RELATED APPLICATIONS

This application is a U.S. National Phase application under 35 U.S.C. § 371 of PCT Application No. PCT/US2003/25679, filed Aug. 18, 2003, which claims priority under 35 U.S.C. § 119 from US Application No. 60/404,843, filed Aug. 21, 2002.

BACKGROUND OF THE INVENTION

The present invention relates to processes for the preparation of 3-chloromethyl-1,2,4-triazolin-5-one (I), which is useful as an intermediate in the manufacture of the pharmaceutical compound 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine. This compound and related compounds are described in PCT International Patent Publication WO95/16679 and U.S. Pat. No. 5,637,699.

The preparation of of 3-chloromethyl-1,2,4-triazolin-5-one (I) has been disclosed, see for example International patent specification WO01/96315, published Dec. 20, 2001, and Cowden, et al., *Tetrahedron Letters*, 2000, vol. 41, 8661. One of the previously reported methods for making (I) involves a one pot reaction of semicarbazide hydrochloride (III•HCl) with a methyl orthoester (II) in an alcoholic solvent.

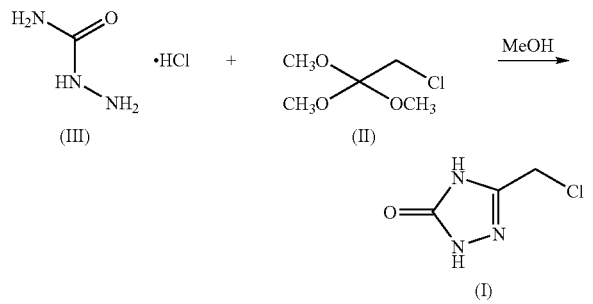

The general process for the preparation of triazolinone (I) as conventionally described above stirs a mixture of the hydrochloride salt of semicarbazide (III•HCl) and orthester (II) at room temperature in methanol for about 3 days. The methanol is evaporated, and (I) is precipitated with toluene. This reaction, although simple and straightforward, is very time consuming for large scale or industrial use. Moreover, the inventors of the present invention noted decomposition of the orthoester (II) in studies of the reaction mixture. Attempts to elevate the temperature to accelerate the reaction increased the decomposition of (II).

It will be appreciated that compound (I) is is an important intermediate for a particularly useful and promising class of therapeutic agents. As such, optimized reaction conditions for compound (I), applicable to large scale or industrial manufacture, are highly desirable.

In accordance with the present invention, the use of alkyl or aryl sulfonic acid salts of semicarbazide (III), especially the methanesulfonic (mesylate) or para-toluenesulfonic (tosylate) salts of (III), surprisingly results in improved reaction yields, shorter reaction times, no detectable decomposition of orthoester (II), and greater purity of the final product. Moreover, by the use of sulfonic acid salts as described herein, it is possible to elevate the reaction temperature. Additionally, the reaction time is reduced considerably compared to conventional routes to triazolinone (I). Despite the aforementioned benefits of the use of sulfonic acid salts of semicarbazide (III) for this process, the use of these salts for this purpose has not previously been disclosed. Additionally, the mesylate and tosylate salts of semicarbazide (III) have not previously been disclosed in substantially pure form.

Accordingly, the present invention describes a superior method for the manufacture of 3-chloromethyl-1,2,4-triazolin-5-one (I), via a simple, short, and efficient synthesis.

SUMMARY OF THE INVENTION

The novel process of this invention involves the use of alkyl or aryl sulfonic acid salts of semicarbizide (III) in the synthesis of 3-chloromethyl-1,2,4-triazolin-5-one (I), according to the reaction scheme:

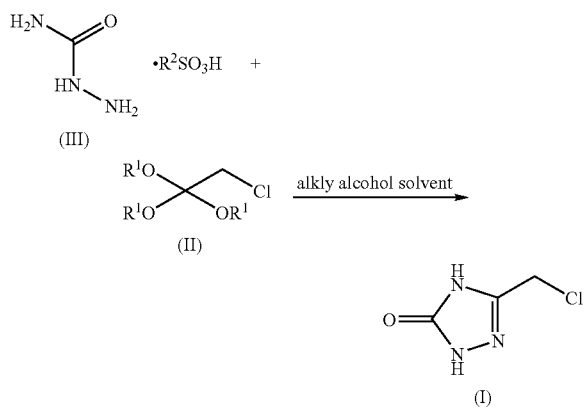

wherein each $R^1$ independently represents $C_{1-10}$alkyl or aryl, and $R^2$ is a $C_{1-10}$alkyl $C_{1-10}$alkylhalo, $C_{5-16}$cycloalkyl, or aryl group, especially with $R^2$ as methyl or para-toluenyl. The use of the alkyl or aryl sulfonyl salts of (III) allows the reaction to be run at elevated temperature, and results in less decomposition of starting materials, faster reaction times, and greater purity than previously disclosed methods for preparing (I).

Compound (I) is is an important intermediate in the synthesis of therapeutic agents. As such, optimized reaction conditions for compound (I), applicable to large scale or industrial manufacture, are highly desirable.

Another novel process described herein is the preparation of the mesyl and tosyl salts of (III). Also the alkyl and aryl sulfonic acid salts of (III) in a pure state have not previously been disclosed.

DETAILED DESCRIPTION OF THE INVENTION

The present invention relates to a process for preparing of 3-chloromethyl-1,2,4-triazolin-5-one, of formula (I):

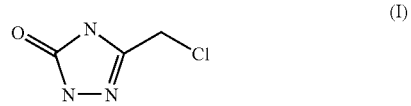

comprising reacting a triaryl- or trialkylorthoester of formula (II):

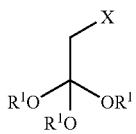

wherein X is a halide, and each $R^1$ independently is a $C_{1-10}$alkyl or aryl, with a sulfonic acid salt of semicarbazide of formula (III):

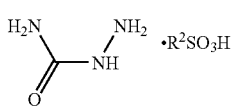

wherein $R^2$ is a $C_{1-10}$alkyl, $C_{1-10}$alkylhalo, $C_{5-16}$cycloalkyl, or aryl, and wherein said reaction is performed in an organic solvent, and wherein the resultant compound of formula (I) is collected.

In an embodiment of this invention, $R^2$ of the sulfonic acid salt of semicarbazide (III) comprises an alkyl group, such as methyl, ethyl, propyl, and the like. In the case where $R^2$ is methyl, the sulfonic acid is methanesulfonic acid. Alternatively, $R^2$ of the sulfonic acid salt of semicarbazide (III) comprises an alkylhalo group, such as trifluoromethyl, in which case the sulfonic acid is trifluoromethane-sulfonic acid (triflic acid). In another alternative, $R^2$ of the sulfonic acid salt of semicarbazide (III) comprises a cycloalkyl group. Cycloalkyl groups with a wide variety of substitution can give the desired result, but a specific example is camphor-10-yl, in which case the sulfonic acid is camphor-10-sulfonic acid. In another alternative, $R^2$ of the sulfonic acid salt of semicarbazide (III) comprises an aryl group. Specific aryl groups that give good results are phenyl or para-tolyl, in which case the sulfonic acids are, respectively, benzenesulfonic acid or para-toluenesulfonic acid.

A solvent for this reaction comprises an alkyl alcohol, such as methanol, but ethanol, propanol, and the like also give the desired result.

An embodiment of $R_1$ of (II) is methyl, although other alkyl or aryl embodiments, such as phenyl, give the desired result. An embodiment of X in (II) is chloride, although other halides give the desired result.

By the use of alkyl or aryl sulfonic acid salts of (III) as described herein, the reaction can be run successfully at elevated temperatures, in the range of about 20–70° C., with the preferred temperature range about 30–50° C., and the most preferred temperature range is about 35–45° C.

In the subject process, the reaction is generally complete in a time of about 1–24 hours, with a preferred reaction time of about 5–20 hours, and a most preferred reaction time of about 10–16 hours.

In an embodiment of the present invention, the product is collected by concentration of the reaction mixture, addition of an ethereal solvent such as MTBE, cooling, filtering, washing the cake with an ethereal solvent such as MTBE, contacting the cake with aqueous acid for several hours, such as about 1–6 hours, and filtering the liquids to isolate the final product as a solid. In one embodiment of this collection, the aqueous acid is about 0.5 to 5 N hydrochloric acid. Alternatively, the aqueous acid is about 0.5 to 5 N trifluoroacetic acid.

In another embodiment of the present invention, the product is collected by concentration of the reaction mixture, addition of a brine solution, additional concentration of the mixture, cooling, filtering, contacting the resulting cake with an aqueous acid for several hours, such as about 1–6 hours, and filtering the liquids to isolate the final product as a solid. An embodiment of the brine solution is an aqueous sodium chloride solution. In one embodiment of this collection, the aqueous acid is about 0.5 to 5 N hydrochloric acid. Alternatively, the aqueous acid is about 0.5 to 5 N trifluoroacetic acid.

An alternate embodiment relates to a process for preparing of 3-chloromethyl-1,2,4-triazolin-5-one, of formula (I):

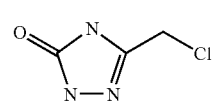

comprising reacting a triaryl- or trialkylorthoester of formula (II):

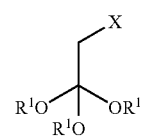

wherein X is a halide, and each $R^1$ independently is a $C_{1-10}$alkyl or aryl, with a an acid salt of semicarbazide of formula (II):

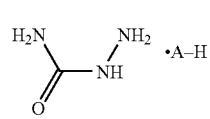

wherein A-H is an acid that provides a non-coordinating weakly basic counterion, such as an acid selected from the group consisting of trifluoracetic acid, phosphoric acid, phosphorous acid, boronic acid, tetraphenyl borate, phenyl boronic acid, napthyl boronic acid, and wherein said reaction is performed in an organic solvent, and wherein the resultant compound of formula (I) is collected.

An additional embodiment of the present invention is directed to the alkyl and aryl sulfonic acid salts of semicarbazide (III), which have not previously been disclosed as substantially pure compounds:

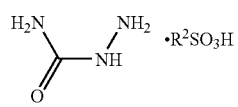

wherein $R^2$ is a $C_{1-10}$alkyl, $C_{1-10}$alkylhalo, $C_{5-16}$cycloalkyl, or aryl. The mesylate salt of (III) has not been described previously at all, and the tosylate salt of (III) has only been mentioned generically in U.S. Pat. No. 2,749,217 (granted Jun. 5, 1956), without experimental detail, and without being isolated, purified, or exemplified. Claim 1 of the aforementioned U.S. patent discloses the possibility that the tosylate salt can be made, but indicates that it is part of a "reaction mixture" (cf. col. 10, line 20), and makes no disclosure whatsoever to the pure or isolated compound.

In an embodiment of this invention, $R^2$ of the sulfonic acid salt of semicarbazide (III) comprises an alkyl group, such as methyl, ethyl, propyl, and the like. In the case where $R^2$ is methyl, the sulfonic acid is methanesulfonic acid. Alternatively, $R^2$ of the sulfonic acid salt of semicarbazide (III) comprises an alkylhalo group, such as trifluoromethyl, in which case the sulfonic acid is trifluoromethanesulfonic acid (triflic acid). In another alternative, $R^2$ of the sulfonic acid salt of semicarbazide (III) comprises a cycloalkyl group. Cycloalkyl groups with a wide variety of substitution can give the desired result, but a specific example is camphor-10-yl, in which case the sulfonic acid is camphor-10-sulfonic acid. In another alternative, $R^2$ of the sulfonic acid salt of semicarbazide (III) comprises an aryl group. Specific aryl groups that give good results are phenyl or para-tolyl, in which case the sulfonic acids are, respectively, benzenesulfonic acid or para-toluenesulfonic acid.

In accordance with the present invention, the alkyl and aryl sulfonate salts of semicarbazide (III) are particularly advantageous in the preparation of triazolinone (I), and new methods for efficiently preparing these salts are described herein. Other semicarbazide salts have previously been prepared typically by the method of Michael, *J. Am. Chem. Soc.*, 1919, vol 41, 393, by treating an aqueous solution of semicarbazide hydrochoride with aqueous sodium hydroxide, pumping off the water at 100° C., repeatedly extracting the residue with hot alcohol, and multiple recrystallizations to obtain semicarbazide free base. Addition of acids, such as sulfuric acid or acetic acid, to an aqueous solution of semicarbazide free base yielded various salts. The problems of water removal, extraction with hot methanol, and multiple recrystallizations to obtain the free base are obviated by the methods reported herein.

An alternative method used previously to generate semicarbazide free base is that of Audrieth, J. Am. Chem. Soc., 1930, vol 52, 1250, who treated the sulfate salt of semicarbazide with liquid ammonia or barium hydroxide. These methods also are far less amenable to industrial manufacture than the methods reported herein.

An alternate embodiment of the present invention is directed to a process for the preparation of a sulfonic acid salt of semicarbazide (III):

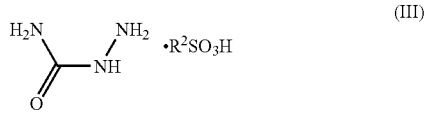

(III)

wherein $R^2$ is a $C_{1-10}$alkyl, $C_{1-10}$alkylhalo, $C_{5-16}$cycloalkyl, or aryl, comprising:

adding a solution of ammonia in a first alcoholic solvent to a slurry of semicarbazide hydrochloride suspended in a second alcoholic solvent, filtering off the resulting ammonium chloride, diluting the filtrate with an organic solvent, treating the solution so obtained with a slight molar excess of an alkyl or aryl sulfonic acid, and collecting the semicarbazide salt.

In an embodiment of this invention, $R^2$ of the sulfonic acid salt of semicarbazide (III) comprises an alkyl group, such as methyl, ethyl, propyl, and the like. In the case where $R^2$ is methyl, the sulfonic acid is methanesulfonic acid. Alternatively, $R^2$ of the sulfonic acid salt of semicarbazide (III) comprises an alkylhalo group, such as trifluoromethyl, in which case the sulfonic acid is trifluoromethanesulfonic acid (triflic acid). In another alternative, $R^2$ of the sulfonic acid salt of semicarbazide (III) comprises a cycloalkyl group. Cycloalkyl groups with a wide variety of substitution can give the desired result, but a specific example is camphor-10-yl, in which case the sulfonic acid is camphor-10-sulfonic acid. In another alternative, $R^2$ of the sulfonic acid salt of semicarbazide (III) comprises an aryl group. Specific aryl groups that give good results are phenyl or para-tolyl, in which case the sulfonic acids are, respectively, benzenesulfonic acid or para-toluenesulfonic acid.

For the preparation of the semicarbazide sulfonic acid salts (III), the first, second, or both alcoholic solvents are methanol. Other alkyl alcohol solvents, such as ethyl, propyl, iso-propyl alcohols, and the like, also give the desired result. The organic solvent should be immiscible with water. For example, ethyl acetate, methylene chloride, methyl t-butyl ether, toluene, and the like, are desirable solvents.

It will be appreciated that the aforementioned process for the preparation of semicarbazide (III) relies upon inexpensive starting materials, readily handled reagents and solvents, and does not require temperatures as high as those described previously, and does not require recrystallizations to obtain a pure product. In this process, the semicarbazide salts precipitate in substantially pure form from the organic solution and are collected by simple filtration. Further, this process is amenable to industrial scale manufacture of the alkyl and aryl sulfonic acid salts of semicarbazide.

As appreciated by those of skill in the art, the terms "halo" or "halogen" as used herein are intended to include chloro, fluoro, bromo and iodo. The term "halide" is intended to include chloride, fluoride, bromide, or iodide. The term "$C_{1-10}$alkyl" is defined to identify an alkyl group as having 1 to 10 carbons in a linear or branched arrangement, such that "$C_{1-10}$alkyl" specifically includes methyl, ethyl, n-propyl, iso-propyl, n-butyl, iso-butyl, tert-butyl, and other simple 1 to 10 carbon alkyl groups. The term "$C_{1-10}$alkylhalo" is defined to identify alkyl groups as defined above with one or more halogen atoms on one or carbon atoms in the alkyl group. This term specifically includes trifluoromethyl. The term "$C_{5-16}$cycloalkyl" as used herein refers to a cyclic alkyl group comprising from 5 to 16 carbon atoms in the ring, and includes such systems with simple substitution, such as alkyl, halo, carbonyl, ester, etc., and specifically includes camphor. The term "aryl" as used herein is intended to include phenyl, napthyl, toluenyl, mesityl, and the aforementioned chemical groups with simple halo or alkyl substitution. The term "MTBE" refers to methyl t-butyl ether. The term "CSA" refers to camphor-10-sulfonic acid. The term "TFA" refers to trifluoroacetic acid. The term "triflic" refers to trifluoromethylsulfonic. The term "mesyl" refers to methanesulfonic. The term "tosyl" refers to para-toluenesulfonic. The term "substantially pure" refers to a chemical compound present in isolated form, with a purity of greater than or equal to 90%, preferably greater than 95% purity.

The following examples are provided by way of illustration only, and in no way are meant to limit the scope of the invention.

EXAMPLE 1a

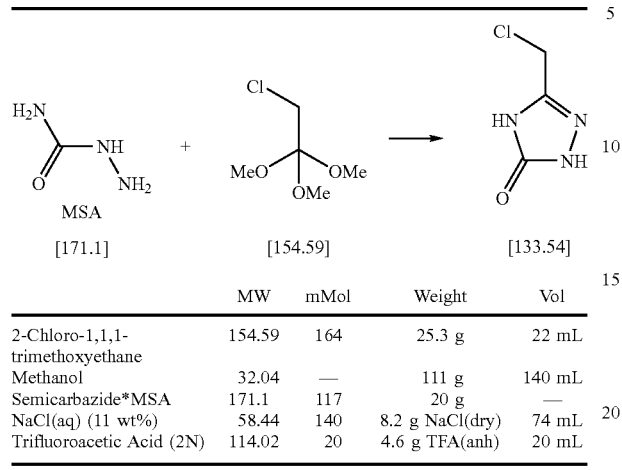

| | MW | mMol | Weight | Vol |
|---|---|---|---|---|
| 2-Chloro-1,1,1-trimethoxyethane | 154.59 | 164 | 25.3 g | 22 mL |
| Methanol | 32.04 | — | 111 g | 140 mL |
| Semicarbazide*MSA | 171.1 | 117 | 20 g | — |
| NaCl(aq) (11 wt%) | 58.44 | 140 | 8.2 g NaCl(dry) | 74 mL |
| Trifluoroacetic Acid (2N) | 114.02 | 20 | 4.6 g TFA(anh) | 20 mL |

Semicarbazide.MSA salt was charged to a 250 mL round bottom flask. 2-chloro-1,1,1-trimethoxyethane (22 mL, 25.3 grams) was charged to the reactor and the resulting slurry was agitated using an overhead stirrer. The reactor temperature is raised to 38–42° C., and was agitated for 16 h. The resulting solution was concentrated under vacuum to a final volume of 50 mL. Aqueous sodium chloride solution (74 ml) was charged to the reactor, at which time the vacuum concentration continues to a final volume of 50 ml, maintaining the temperature between 25 and 35° C. during the concentration. The slurry was cooled to 0° C. and aged for a minimum of 1 hour, at which time the slurry was filtered. The resulting wet cake was washed with either 2N HCl or 2N TFA and dried under full vacuum at 40–50° C.

EXAMPLE 1b

Synthesis of of 3-chloromethyl-1,2,4-triazolin-5-one (I) with semicarbazide mesylate

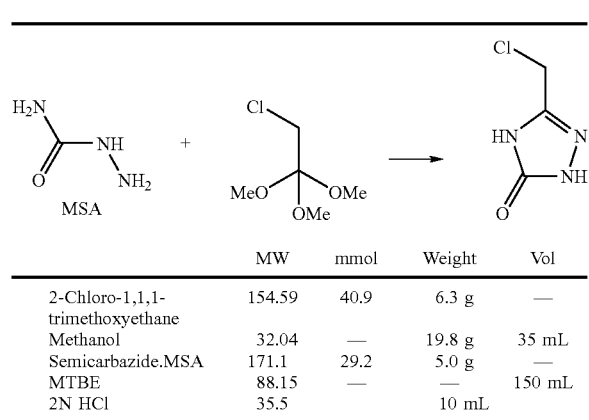

| | MW | mmol | Weight | Vol |
|---|---|---|---|---|
| 2-Chloro-1,1,1-trimethoxyethane | 154.59 | 40.9 | 6.3 g | — |
| Methanol | 32.04 | — | 19.8 g | 35 mL |
| Semicarbazide.MSA | 171.1 | 29.2 | 5.0 g | — |
| MTBE | 88.15 | — | — | 150 mL |
| 2N HCl | 35.5 | — | — | 10 mL |

A mixture of semicarbazide.MSA (5.0 g, 29.2 mmol), 2-chloro-1,1,1-trimethoxyethane (Chloroorthoester, 6.3 g, 40.9 mmol) and methanol (35 mL) was stirred at 38–42° C. for 12 hours. The reaction was then concentrated to a volume of 20 n L. A constant volume distillation at 20 mL was done while adding 40 mL of MTBE. This was repeated until a target solvent composition of 95% MTBE/5% MeOH was obtained. The reaction was then cooled to 0° C., aged for 1 hour, and then filtered. The cake was washed with MTBE (10 mL). The white solid was swished with 2N HCl (10 mL) on the filter for 3h. After filtration, the solids are dried at 40° C. in vacuo.

EXAMPLE 2

Synthesis of of 3-chloromethyl-1,2,4-triazolin-5-one (I) with semicarbazide tosylate

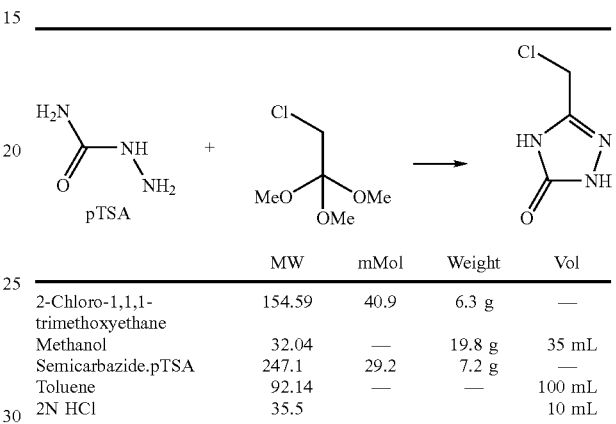

| | MW | mMol | Weight | Vol |
|---|---|---|---|---|
| 2-Chloro-1,1,1-trimethoxyethane | 154.59 | 40.9 | 6.3 g | — |
| Methanol | 32.04 | — | 19.8 g | 35 mL |
| Semicarbazide.pTSA | 247.1 | 29.2 | 7.2 g | — |
| Toluene | 92.14 | — | — | 100 mL |
| 2N HCl | 35.5 | — | — | 10 mL |

A mixture of semicarbazide.pTSA (7.2 g, 29.2 mmol), 2-chloro-1,1,1-trimethoxyethane (6.3 g, 40.9 mmol) and methanol (35 mL) was stirred at 38–42° C. for 12 hours. The reaction was then concentrated to a volume of 20 mL. A constant volume distillation at 20 mL was done while adding 40 mL of toluene. This was repeated until a target solvent composition of 99% Toluene/1% MeOH was obtained. The reaction was then cooled to 0° C., aged for 1 hour, and then filtered. The cake was washed with toluene (10 mL). The white solid was swished with 2N HCl (10mL) on the filter for 3h. After filtration, the solids are dried at 40° C. in vacuo.

EXAMPLE 3

Synthesis of semicarbazide mesylate

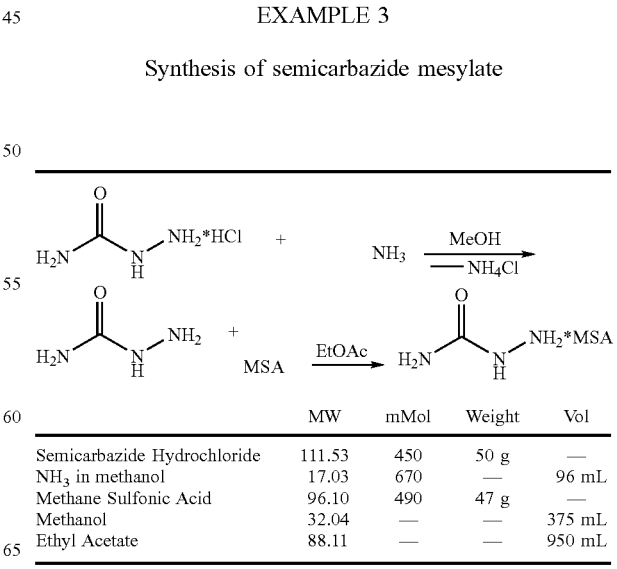

| | MW | mMol | Weight | Vol |
|---|---|---|---|---|
| Semicarbazide Hydrochloride | 111.53 | 450 | 50 g | — |
| $NH_3$ in methanol | 17.03 | 670 | — | 96 mL |
| Methane Sulfonic Acid | 96.10 | 490 | 47 g | — |
| Methanol | 32.04 | — | — | 375 mL |
| Ethyl Acetate | 88.11 | — | — | 950 mL |

At room temperature, NH₃ (96 mL, 670 mmol, 7N in methanol) was added subsurface via syringe to a stirred slurry of semicarbazide hydrochloride (50 g, 450 mmol) in methanol (375 mL). After one hour, the solution was filtered to remove ammonium chloride. The filtrate was diluted with ethyl acetate (750 mL) and the resulting solution was concentrated to ~400 mL by a reduced pressure distillation. The solution was filtered and treated with methane sulfonic acid (47.4 g, 490 mmol). Upon acid addition, a white precipitate formed which was collected by filtration. The solid was rinsed with ethyl acetate (200 mL) and dried under reduced pressure.

EXAMPLE 4

Synthesis of semicarbazide tosylate

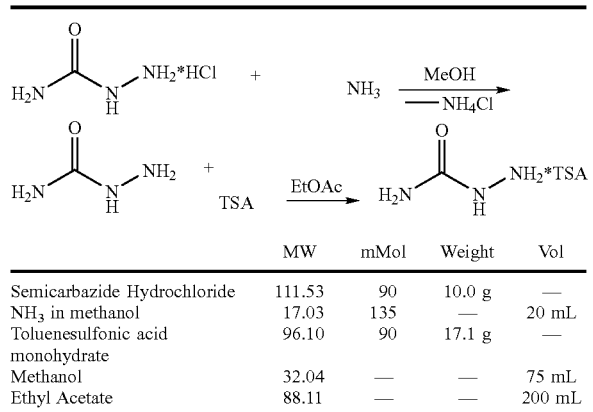

| | MW | mMol | Weight | Vol |
|---|---|---|---|---|
| Semicarbazide Hydrochloride | 111.53 | 90 | 10.0 g | — |
| NH₃ in methanol | 17.03 | 135 | — | 20 mL |
| Toluenesulfonic acid monohydrate | 96.10 | 90 | 17.1 g | — |
| Methanol | 32.04 | — | — | 75 mL |
| Ethyl Acetate | 88.11 | — | — | 200 mL |

At room temperature, NH₃ (20 mL, 135 mmol, 7N in methanol) was added subsurface via syringe to a stirred slurry of semicarbazide hydrochloride (10.0 g, 90 mmol) in methanol (75 mL). After one hour, the solution was filtered to remove ammonium chloride. The filtrate was diluted with ethyl acetate (150 mL) and the resulting solution was concentrated to ~300 mL by a reduced pressure distillation. The solution was filtered and treated with toluene sulfonic acid (17.1 g, 90 mmol). Upon acid addition, a white precipitate formed which was collected by filtration. The solid was rinsed with ethyl acetate (50 mL) and dried under reduced pressure.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A process for the preparation of a compound 3-chloromethyl-1,2,4-triazolin-5-one of formula (I):

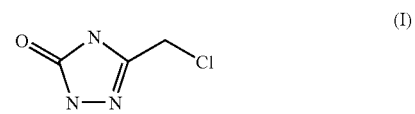

comprising reacting a triaryl- or trialkyl-orthoester of formula (II):

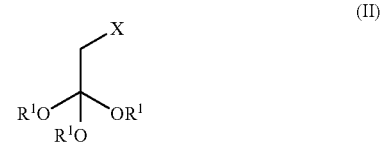

wherein X is chloro, and each $R^1$ independently is independently selected from $C_{1-10}$alkyl, and phenyl which is unsubstituted or substituted with halo or $C_{1-6}$alkyl, with a sulfonic acid salt of semicarbazide of formula (III):

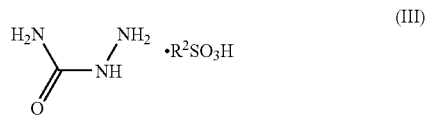

wherein $R^2$ is independently selected from $C_{1-10}$alkyl, $C_{1-10}$alkylhalo, $C_{5-16}$cycloalkyl, and phenyl which is unsubstituted or substituted with halo or $C_{1-6}$alkyl, in an organic solvent, and collecting the compound of formula (I).

2. The process of claim 1 wherein the sulfonic acid salt of formula (III), $R^2$ is methyl.

3. The process of claim 1 wherein the sulfonic acid salt of formula (III), $R^2$ is trifluoromethyl.

4. The process of claim 1 wherein the sulfonic acid salt of formula (III), $R^2$ is camphor-10-yl.

5. The process of claim 1 wherein the sulfonic acid salt of formula (III), $R^2$ is para-tolyl.

6. The process of claim 1 wherein the organic solvent comprises an alkyl alcohol.

7. The process of claim 6 wherein the organic solvent comprises methanol.

8. The process of claim 1 wherein the orthoester of formula (II), each $R^1$ is methyl.

9. The process of claim 1 wherein the orthoester of formula (II), each $R^1$ is phenyl.

10. The process of claim 1 wherein the reaction temperature is maintained at about 20–70° C.

11. The process of claim 1 wherein the reaction temperature is maintained at about 35–45° C.

12. The process of claim 1 wherein the collection of the compound of formula (I) comprises the steps of:
concentrating the reaction mixture,
adding a brine solution to the concentrated reaction mixture,
cooling the mixture to form a solid product, isolating the solid product,
contacting the solid product with an aqueous acid for about 1–6 hours,
and isolating the compound of formula (I).

13. The process of claim 12, wherein the brine solution comprises an aqueous sodium chloride solution.

14. The process of claim 12, wherein the aqueous acid comprises about 0.5 to 5 N hydrochloric acid.

15. The process of claim 12, wherein the aqueous acid comprises about 0.5 to 5 N trifluoroacetic acid.

* * * * *